(12) United States Patent
Ueno et al.

(10) Patent No.: US 7,511,277 B2
(45) Date of Patent: Mar. 31, 2009

(54) NUCLEAR MEDICINE DIAGNOSTIC APPARATUS, POSITRON EMISSION COMPUTED TOMOGRAPHY APPARATUS, AND DETECTOR UNITS

(75) Inventors: Yuuichirou Ueno, Hitachi (JP); Takafumi Ishitsu, Hitachi (JP); Keiji Kobashi, Mito (JP); Kensuke Amemiya, Hitachinaka (JP); Katsutoshi Tsuchiya, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 48 days.

(21) Appl. No.: 11/524,919

(22) Filed: Sep. 22, 2006

(65) Prior Publication Data

US 2007/0080296 A1    Apr. 12, 2007

(30) Foreign Application Priority Data

Sep. 30, 2005    (JP)    ............... 2005-289262

(51) Int. Cl.
*G01T 1/161*    (2006.01)
(52) U.S. Cl. ............... 250/363.08; 250/363.04; 250/363.05; 250/370.15
(58) Field of Classification Search ............ 250/363.02, 250/363.03, 363.05, 370.09, 370.15
See application file for complete search history.

(56) References Cited

U.S. PATENT DOCUMENTS 6,586,744 B1 * 7/2003 Griesmer et al. ....... 250/370.15
6,988,827 B2 * 1/2006 Mueller .................. 378/199
7,065,173 B2 * 6/2006 Lacey et al. .............. 378/19
2005/0151087 A1 * 7/2005 Ueno et al. ............ 250/370.09

FOREIGN PATENT DOCUMENTS

| JP | 10-160847 | 6/1998 |
|---|---|---|
| JP | 2001-245878 | 9/2001 |
| JP | 2003-194951 | 7/2003 |
| JP | 2005-128000 | 5/2005 |
| JP | 2005-201671 | 7/2005 |

* cited by examiner

*Primary Examiner*—David P Porta
*Assistant Examiner*—Casey Bryant
(74) *Attorney, Agent, or Firm*—Mattingly, Stanger, Malur & Brundidge, PC

(57) ABSTRACT

A nuclear medicine diagnostic apparatus is provided that can improve time resolution and energy resolution and diagnosing accuracy by enhancing radiation detectors in terms of moisture-proofing and dust-proofing effects while efficiently cooling the radiation detectors. The apparatus has a first region A in which radiation detectors are to be accommodated, and a second region B in which signal processors are to be accommodated. These regions are provided inside a housing member 5 via an adiabatic member 7. The housing member 5 also has a ventilation port 8 formed to communicate with the first region A and equipped with an anti-dust filter. Ventilation holes 34 are formed to communicate with the first region B and serving as entrances for cooling air. Unit fans 33 serve as exits for the cooling air.

24 Claims, 7 Drawing Sheets

NUCLEAR MEDICINE DIAGNOSTIC APPARATUS, POSITRON EMISSION COMPUTED TOMOGRAPHY APPARATUS, AND DETECTOR UNITS

BACKGROUND OF THE INVENTION

The present invention relates generally to nuclear medicine diagnostic apparatuses that use radiation. More particularly, the invention concerns a nuclear medicine diagnostic apparatus, positron emission computed tomography (PET) apparatus, and detector unit group suitable for performing multiple types of radiation examinations such as X-ray CT, PET, and single-photon emission computed tomography (SPECT).

The examination techniques that use radiation can be used to examine the insides of target bodies in a non-invasive fashion. Radiation examination techniques for human bodies, in particular, include, for example, X-ray CT, PET, and SPECT. All these techniques are intended to acquire images by measuring the physical quantities of a body to be examined, as integral data of radiation in the emission direction thereof, then back-projecting the integral data, and calculating the physical quantities of individual voxels within the target body. These techniques require processing vast volumes of data, and the rapid development of computer technology in recent years has enabled techniques to provide detailed images rapidly and at high resolution.

The PET and SPECT apparatuses used for diagnosis in nuclear medicine employ a technique that allows detection of the functional activity and metabolism at a molecular biological level that are not detectable with other diagnostic apparatuses such as an X-ray CT apparatus. The PET and SPECT apparatuses can provide functional images of target bodies, such as human bodies.

PET is a technique for acquiring images by administering to humans radioactive pharmaceuticals labeled with a positron emission nuclide such as $^{18}$F, $^{15}$O, or $^{11}$C, and measuring the distribution of the pharmaceutical. The types of pharmaceuticals used include, for example, 2-[F-18] fluoro-2-deoxy-D-glucose ($^{18}$FDG), which is used to identify a tumor site by utilizing the characteristic that the pharmaceutical densely accumulates at the tumor tissue by means of glucose metabolism. The radionuclide that has been introduced into the human body decays and emits a positron ($\beta$+). Upon combining with an electron and decaying, the emitted positron itself emits one pair of annihilations (annihilation pair) having an energy of 511 keV. Since the two annihilations are irradiated in essentially opposite directions at 180±0.6 degrees, projection data can be obtained by simultaneously detecting the annihilations using multiple radiation detectors arranged around the target body, and storing radial data thereof. Back-projection of the projection data by using a filtered back-projection method, or the like, makes it possible to identify radiation positions, that is, the accumulating positions of the radionuclide.

SPECT is a technique for acquiring images by administering to target bodies, such as human bodies, a radioactive pharmaceutical labeled with a single-photon emission nuclide, and measuring the distribution of the pharmaceutical. A single $\gamma$-ray with an energy of about 100 kev is emitted from the pharmaceutical, and the energy of the emitted single $\gamma$-ray is measured using a radiation detector. The emission direction of the single $\gamma$-ray cannot be identified from its energy data measurements. For SPECT, therefore, a collimator is inserted in front of a radiation detector and the single $\gamma$-ray is detected only from a specific direction, whereby projection data can be obtained. As with PET, SPECT uses filtered back-projection or the like to obtain image data by back-projection of projection data. SPECT differs from PET in that because of energy measurement of the single $\gamma$-ray, simultaneous measurement is unnecessary, and hence in that the number of radiation detectors required is small. SPECT is also simple in apparatus configuration.

The above-described conventional PET, SPECT, and other nuclear medicine diagnostic apparatuses use a scintillator(s) as a radiation detector(s) to obtain an image. The scintillator requires converting an incident into visible light and then reconverting the light into an electrical signal via a photomultiplier. The scintillator has also had a problem in that since the number of photons generated during the conversion into visible light is small and since, as described above, two conversion process steps are necessary, energy resolution decreases and this does not always make diagnosing accuracy improvable. This decrease in energy resolution results in quantitative assessment being impossible, particularly during 3D imaging with PET. This is because the decrease in energy resolution necessitates the energy threshold level of the single $\gamma$-ray to be correspondingly reduced and because this results in detection of a large quantity of human body internal scattering which increases noise during 3D imaging.

In recent years, therefore, semiconductor radiation detectors are attracting attention as radiation detectors for use with nuclear medicine diagnostic apparatuses. The semiconductor radiation detectors convert an incident $\gamma$-ray directly into an electrical signal, and feature high energy resolution since a large number of electrons and hole pairs are generated.

The characteristics of these radiation detectors (scintillators and semiconductor radiation detectors) are typically temperature-dependent. The characteristics referred to here include time resolution and energy resolution. It is known that these characteristics improve during the use of the radiation detectors under low-temperature conditions.

Japanese Patent Laid-open No. 2005-128000 (Paragraphs 0058-0060) describes a cooling structure that efficiently cools signal processors and radiation detectors. Maintaining these radiation detectors at low temperature allows the improvement of both image quality and quantitative characteristics, and hence, more accurate diagnosis.

SUMMARY OF THE INVENTION

In addition to temperature, moisture-proofing and dust-proofing capabilities are important in radiation detectors. Semiconductor detectors, in particular, need to be applied with a high-voltage bias. If dust sticks to the detector or the high-voltage sections of its circuit board, the dust increases current leakage and reduces energy resolution and time resolution. In addition, an increase in humidity under such a dusty state further reduces energy resolution and time resolution.

Furthermore, although conventional techniques employ a radiation detector sealing structure to prevent dust from sticking, these techniques have had problems in that the radiation detectors are technically difficult to completely seal due to allowing for their maintenance. In addition, their humidity control is also difficult. Furthermore, the use of an associated apparatus for an extended time correspondingly permits entry of dust.

An object of the present invention is to provide the following: a nuclear medicine diagnostic apparatus and positron emission computed tomography apparatus that can, while cooling radiation detectors efficiently, enhance moisture-proofing and dust-proofing effects of radiation detectors without deteriorating maintainability, and achieve highly accurate diagnosis by improving time resolution and energy resolution; and detector units used with the nuclear medicine diagnostic apparatus and the positron emission computed tomography apparatus.

In order to solve the above problems, a nuclear medicine diagnostic apparatus of the present invention has detector units arranged around a bed on which the human body to be examined is to be held, wherein each of the detector units includes: a plurality of unit substrates each further including a plurality of radiation detectors for detecting radiation, and a plurality of signal processors to each of which an independent detection signal from each of the radiation detectors is input; a housing member having the plurality of unit substrates and segmented into a first region in which the plurality of radiation detectors are disposed, and a second region in which the plurality of signal processors are disposed; and coolant discharging means for introducing a gaseous coolant into the second region in order to cool the plurality of signal processors and discharging the coolant from the second region; the housing member being formed with a ventilation hole to communicate with an exterior of the housing member as well as with the first region, and having an anti-dust filter connected to the ventilation hole.

The nuclear medicine diagnostic apparatus of the present invention is constructed so that each radiation detector is separated from each signal processor and so that while the signal processor is being air-cooled, the radiation detector is ventilated by the ventilation hole having an anti-dust filter. The coolant discharging means is contributive for the radiation detector to suppress heat propagation from the signal processor, a heat-generating element, and thus to suppress a temperature rise of the radiation detector itself. In addition, ventilation holes that enable inflow of air are provided in a section which communicates with the first region in which the radiation detector is provided, and the anti-dust filter is connected to the ventilation holes, thus preventing a flow of dust into the radiation detector. The provision of the ventilation holes having the anti-dust filter facilitates humidity control since humidity is immediately set to a value that has been set from the outside of the apparatus.

According to the present invention, since it is possible to form a structure that implements moisture-proofing and dust-proofing while maintaining each radiation detector at low temperature, time resolution and energy resolution substantially improve and quantitative characteristics also improve. Thus, diagnosing accuracy can be improved.

According to another aspect of this invention, the detector unit is used for radiation examination and has the following: a plurality of substrates each including a plurality of radiation detectors for detecting radiation, and a plurality of signal processors to each of which an independent detection signal from each of the radiation detectors is input, a housing member internally having the plurality of substrates, the housing member being segmented into a first region in which the plurality of radiation detectors are disposed, and a second region in which the plurality of signal processors are disposed, a ventilation hole of the second region, which introduces a gaseous coolant into the second region in order to cool the plurality of signal processors and a ventilation port of the first region, communicates with an exterior of the housing member as well as with the first region.

BRIEF DESCRIPTION OF THE DRAWINGS

Other objects and advantages of the invention will become apparent from the following description of embodiments with reference to the accompanying drawings in which.

DETAILED DESCRIPTION OF THE PREFERRED EMBODIMENT

A nuclear medicine diagnostic apparatus according to a preferred embodiment of the present invention will be described hereunder with reference to FIGS. 1 to 5. Although the nuclear medicine diagnostic apparatus of the present embodiment will be described taking a PET apparatus as an example, the present invention is not limited to the PET apparatus and can be applied to other nuclear medicine diagnostic apparatuses such as a SPECT apparatus.

Figure 1:
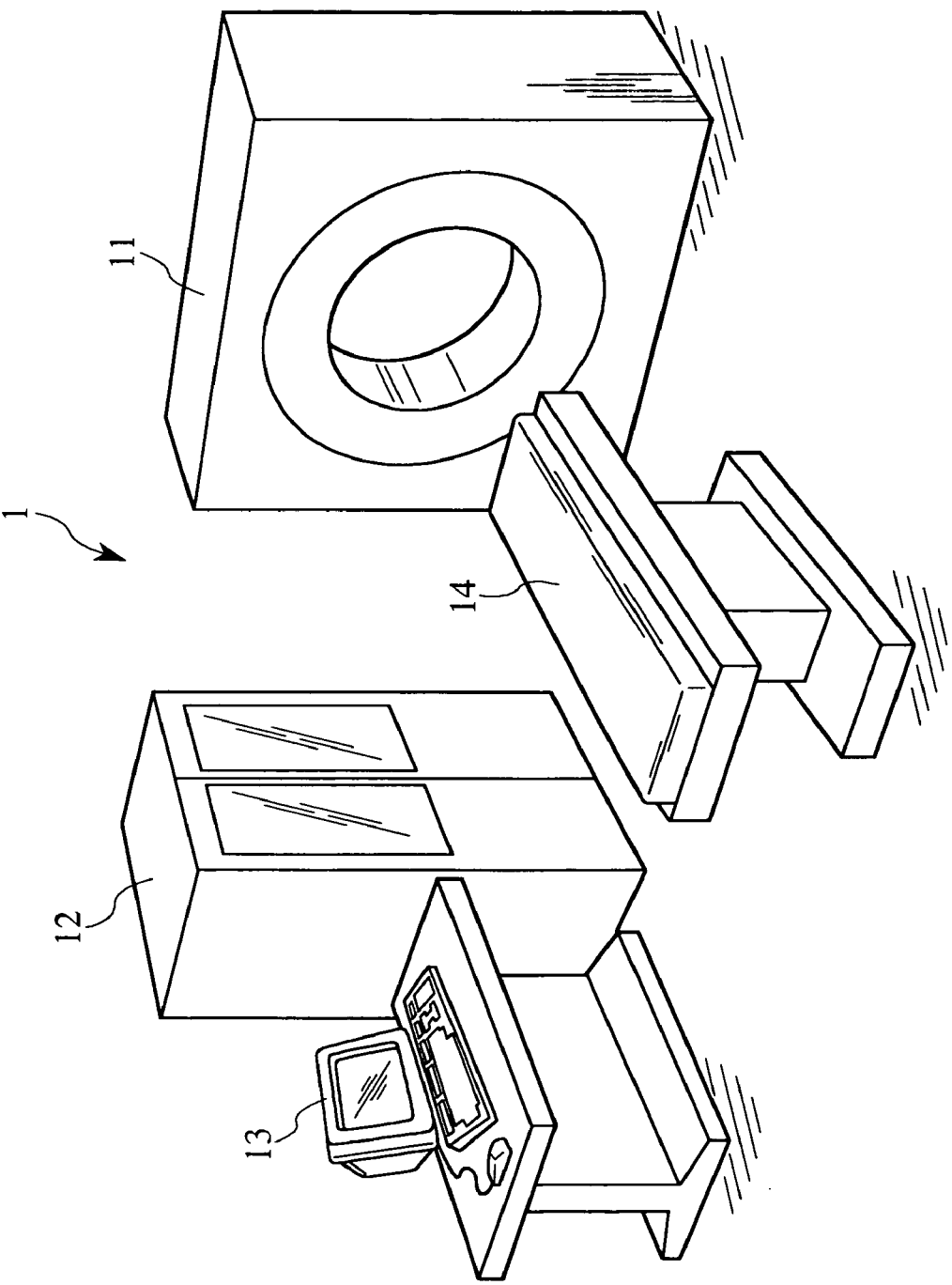
FIG. 1 is a perspective view showing a construction of a nuclear medicine diagnostic apparatus according to an embodiment.

As shown in FIG. 1, PET apparatus 1 (nuclear medicine diagnostic apparatus) includes an image acquisition device 11, a data processor 12 which processes detection data obtained by the image acquisition device 11 during imaging and converts the detection data into image data, a display device 13 which makes a two-dimensional or three-dimensional display of the image data that the data processor 12 outputs, and a bed 14 on which to rest a human body (patient) as a human subject H of examination so as to be movable forward and backward in an body-axis direction.

Figure 2:
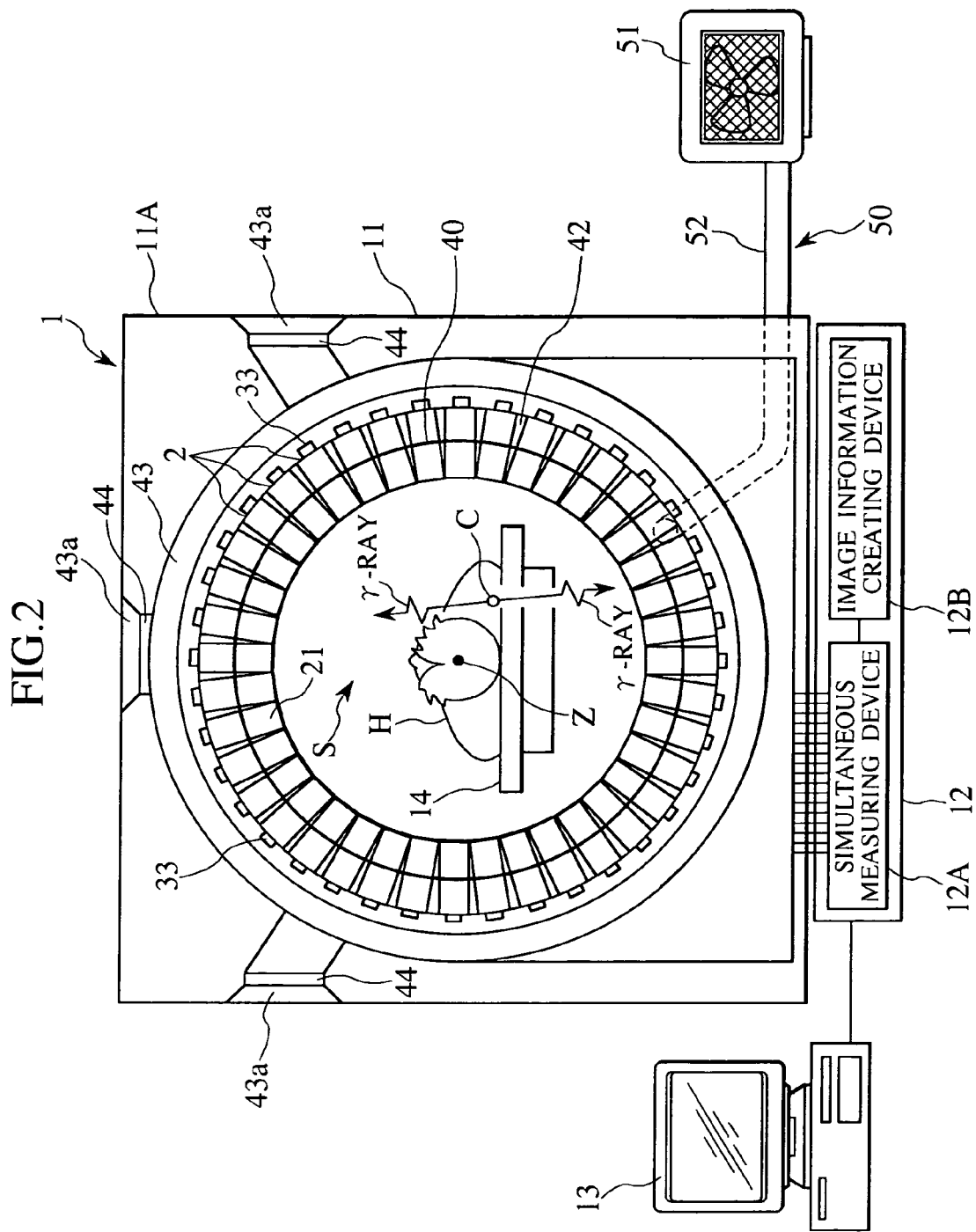
FIG. 2 is a schematic of the circumferential section of an image acquisition device used in FIG. 1.
Figure 3:
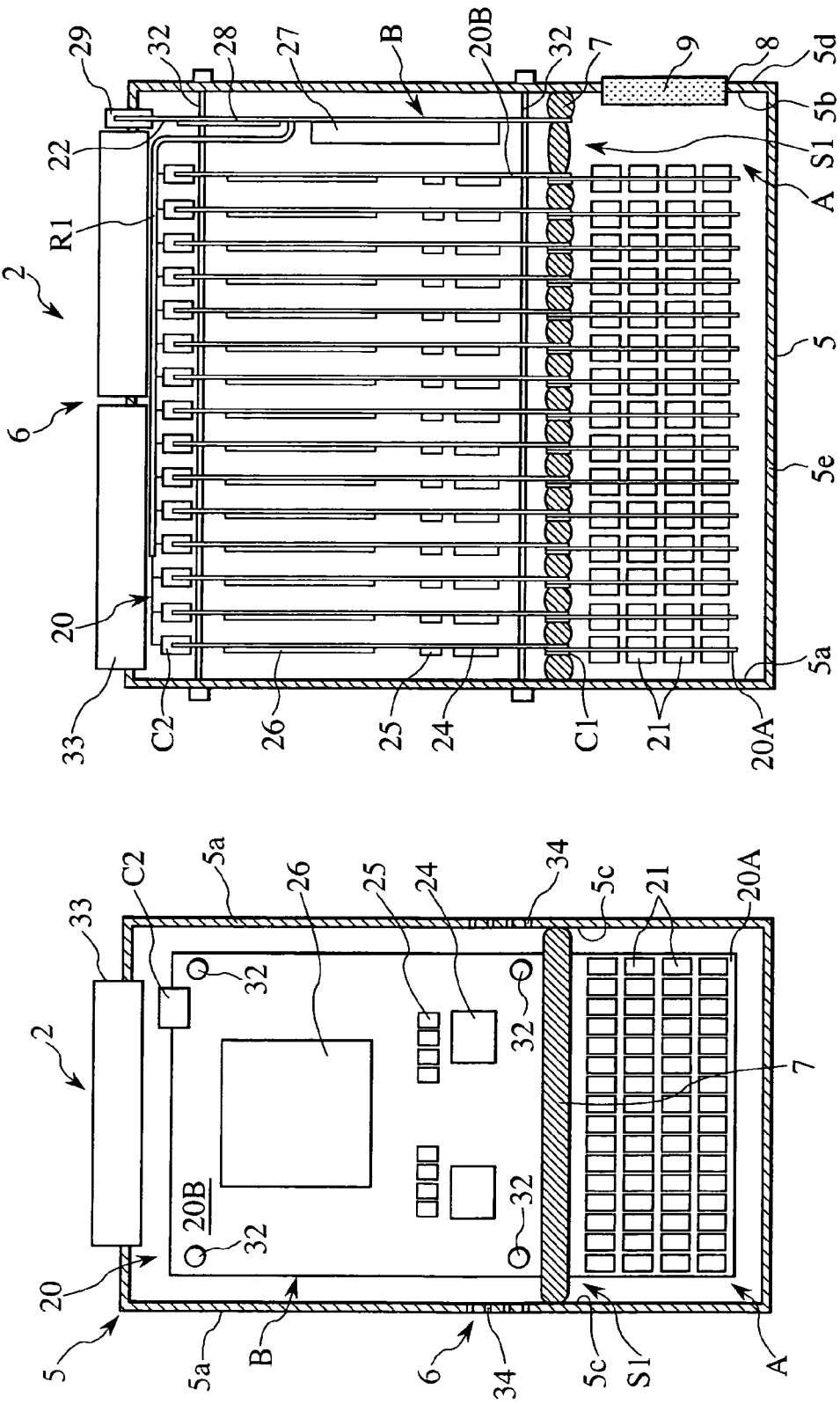
FIG. 3A is a sectional view of a detector unit in the nuclear medicine diagnostic apparatus according to the above embodiment when the detector unit is seen from front.
FIG. 3B is a transverse sectional view of the detector unit.

As shown in FIG. 2, the image acquisition device 11 includes a detector unit 2 having a large number of semiconductor radiation detectors 21 (hereinafter, referred to simply as detectors, details of which will described later herein). This detector unit 2 is disposed inside a casing 11A of the image acquisition device 11, and the detector unit 2 is disposed in large numbers circumferentially with body axis Z of the human subject H as a center so as to encircle the bed 14 that has been inserted into a space S of the image acquisition device 11.

A radioactive pharmaceutical, for example, a fluoro-2-deoxy-D-glucose (FDG) that contains $^{18}F$ whose half-life is 110 minutes is administered to the human subject H. This radioactive pharmaceutical accumulates in a cancer-affected region C, for example. As shown in FIG. 2, one pair of γ-rays (radioactive rays) generated during annihilation of the positron emitted from the FDG are simultaneously emitted from the body interior of the human subject H, in angle directions of 180±0.6 degrees. These γ-rays are detected by two detectors 21 positioned in a 180°-shifted condition in opposite directions. A position from which the γ-rays have originated (i.e., the accumulating section of the radioactive pharmaceutical) in the body of the human subject H is identified from the detection signals output from the detectors 21. The configuration of the detector units 2 and peripheral sections thereof, shown in FIG. 2, is schematically shown to illustrate their arrangement. Their detailed construction will be described later.

The image acquisition device 11 also includes a cooler 50, part of its constituent elements is shown in FIG. 2. The cooler 50 cools each detector unit 2, and in the present embodiment, air is used for cooling (gaseous coolant). Details of the cooler 50 will be described later.

As shown in FIG. 2, the data processor 12 includes a simultaneous measuring device 12A and an image information creating device 12B. The data processor 12 acquires packet data (described later) that is output from an integrated FPGA (Field-Programmable Gate Array) 28 on a coupling substrate 22 built into each detector unit 21 detailed later herein (see FIG. 3B for the packet data and the FPGA 28). The simultaneous measuring device 12A identifies the position of the same originating source of the paired γ-rays, only from γ-ray information among all acquired data, and stores the position information into a storage device not shown. The image information creating device 12B creates PET image information (tomographic image information) of the human subject H from the identified position information and displays the PET image information on the display device 13.

More specifically, the simultaneous measuring device 12A compares γ-ray detection time between plural sets of detection data and judges any two sets of data having a simultaneous measuring time window length of, for example, 10 nanoseconds (ns) or less, as an effective data pair. In addition, the image information creating device 12B accumulates emission direction data of the γ-ray pair from IDs of the detectors 21 of the effective data pair and then creates a PET image from the emission direction data by image reconstruction. The created PET image is then output to the display device 13.

As shown in FIGS. 3A and 3B, each detector unit 2 includes a housing member 5, a coolant discharging element 6, an adiabatic member (partitioning member) 7, and unit substrates 20. Incidentally, the image acquisition device 11 shown in FIG. 2 is constructed to have, for example, 60 to 70 detector units 2 removably arranged in a circumferential direction of the device 11, which facilitates maintenance and inspection.

The unit substrates 20 each include a detector substrate 20A that operates as a first substrate, and multiple detectors 21, and the detectors 21 are arranged in matrix form on both sides of the detector substrate 20A.

Multiple such detector substrates 20A as mentioned above are arranged inside a housing member 5, in a direction of the body axis Z of the human subject H (i.e., a longitudinal direction of the bed 14) shown in FIG. 2. In the present embodiment, as shown in FIG. 3B, 15 detector substrates 20A in all are provided by way of example.

In FIG. 3A, the image acquisition device 11 has a total of 64 detectors 21 per side of each detector substrate 20A, 16 units in the circumferential direction of the device 11 (i.e., a layout direction of the detector units 2) and 4 rows in a radial direction of the device 11 (i.e., a direction orthogonal to the layout direction of the detector units 2). This means that in the present embodiment, the detectors 21 are arranged circumferentially around a central axis of the image acquisition device 11 (almost coaxially with the body axis Z of the human subject H). In addition, the detectors 21 in the present embodiment are arranged densely at small layout pitches to implement high-density mounting of the detectors 21 on the detector substrates 20A. This arrangement makes it possible to improve γ-ray detection efficiency on the detector substrates 20A and reduce an examination time.

The detectors 21 each have a semiconductor member stacked in a sandwiched condition between a cathode and anode not shown. This semiconductor member is constructed of a monocrystal of either cadmium telluride (CdTe), thallium bromide (TlBr), gallium arsenide (GaAs), or the like. The anode and the cathode use either platinum (Pt), gold (Au), indium (In), or the like, as their material(s). Employing the thus-constructed detectors 21 makes it possible to enhance electrical-charge collection efficiency and to increase a semiconductor member—γ-ray interaction (i.e., a numerical count) for increased sensitivity by reducing the quantity of γ-rays passing through. The detectors 21 do not always need to have such a stacked structure and may have a single-layer structure or any other appropriate layer structure.

In the PET apparatus 1 here, as the number of detectors 21 installed is increased, γ-rays can be detected more easily and positioning accuracy during γ-ray detection is raised. Preferably, therefore, the detectors 21 are densely arranged as described above, and as shown in FIG. 5, the detectors 21 are preferably arranged in close proximity to one another in a circumferential direction in the casing 11A (see FIGS. 2 and 5) of the image acquisition device 11. By adopting such a structure, it is possible to enhance position resolution of the image obtained.

In the configuration as described above, each detector 21 detects the 511-keV γ-ray (radiation) used in the PET apparatus 1, and outputs an analog signal (γ-ray detection signal) associated with an energy of the γ-ray (i.e., the energy that has caused the interaction with respect to the semiconductor member).

As shown in FIG. 3B, signal processor substrates 20B each have a substrate connector C2 at one end (upper end), and each of the signal processor substrates 20B and the coupling substrates 22 are electrically connected using an interconnecting line R1 connected via the substrate connector C2.

Integrated circuits (analog ASICs 24, ADCs 25, and a digital ASIC 26) for processing the γ-ray detection signals that have been output from each detector 21 described above are mounted on each signal processor substrate 20B. The analog ASICs 24 function as signal processors in the present embodiment.

One analog ASIC 24 includes 32 sets of analog signal processor circuits (analog signal processors), these circuits each having a slow system and a fast system. Independent analog signal processor circuits are provided for each detector 21, and one analog signal processor circuit is connected to one detector 21. The fast system includes a timing pick-off circuit that outputs a timing signal for identifying γ-ray detection time of day. The slow system has a polarity amplifier (linear amplifier), a band-pass filter (waveform shaper), and a peak hold circuit (wave peak value hold device), which are connected in that order in the system in order to calculate a wave peak value of the detected γ-ray. Incidentally, the slow system is named "slow" because the system needs a certain amount of processing time to calculate a wave peak value. The γ-ray detection signal that has been output from the detector 21 and passed through a capacitor and a resistor is amplified by a charge amplifier and the polarity amplifier. The amplified detection signal is input to the peak hold circuit via the band-pass filter. The peak hold circuit holds a maximum value of detection signals, namely, a wave peak value of a γ-ray detection signal proportional to the energy of the detected γ-ray. One analog ASIC 24 is an LSI constructed of 32 sets of analog signal processor circuits.

These integrated circuits amplify the very weak γ-ray detection signal output from the detector 21, and measure the energy of the detected γ-ray and the detection time of day. An independent detector ID that has been set for the particular detector 21 beforehand is added to measured energy and detection time data, and the measured energy and detection time data is output as packet data (digital data).

Each signal processor substrate 20B described above has a connector C1 at the other end (lower end), and the signal processor substrate 20B is mechanically and electrically connected to the above-described detector substrate 20A via the connector C1. The detector substrate 20A and the signal processor substrate 20B may be removably coupled with each other by means of a screw (not shown), at an overlapping section between both substrates 20A and 20B. Signals from the detector substrate 20A to the signal processor substrate 20B can be transmitted with minimum loss by using the electrical connection structure of the substrates 20A and 20B. Reduced signal loss improves, for example, energy resolution of the detector 21.

Since the detector substrate 20A and the signal processor substrate 20B are interconnected via the connector C1 in this way, these substrates can easily be removed and remounted independently of each other. This means, therefore, that for example, if an abnormality occurs in either detector 21, either analog ASIC 24, or the like, only the abnormal section, that is, only the detector substrate 20A or the signal processor substrate 20B needs to be replaced. Even if part of the substrate becomes abnormal, therefore, it is unnecessary to replace the entire substrate with a new one, and maintenance expenses can be reduced as a result.

The coupling substrate 22 includes a high-voltage power supply 27 which operates as a voltage up-converter for supplying a voltage to each unit substrate 20. The coupling substrate 22 also includes an integrated FPGA (Field-Programmable Gate Array) 28 which integrates the packet data that has been output through the substrate connector C2 of each signal processor substrate 20B. In addition, the coupling substrate 22 includes a data transfer device 29 which transmits the integrated packet data to the data processor 12 shown in FIG. 2. In the present embodiment, the coupling substrate 22 is disposed similarly to the signal processor substrate 20B (unit substrate 20) and located near a rear internal end of the housing member 5 described later herein. The location of the coupling substrate 22 is not limited to the rear internal end of the housing member 5 and may be, for example, a front end of the housing member 5.

The high-voltage power supply 27 is connected to a low-voltage power supply (not shown) that is installed outside the image acquisition device 11, and the high-voltage power supply 27 increases a low voltage to 300 V via a DC-DC converter and supplies the 300-V voltage to each detector 21. Also, since the high-voltage power supply 27 is mounted on the coupling substrate 22 and disposed inside the housing member 5, the high-voltage power supply 27 can be easily installed in the image acquisition device 11 by installing the detector unit 2 in a unit-supporting section 40 (see FIG. 2). While, in the present embodiment, each detector 21 in the image acquisition device 11 is disposed to face in a longitudinal direction of the bed 14, the present invention is not limited to this structure and, for example, each detector may be disposed to face in a circumferential direction of the image acquisition device 11.

The unit substrate 20 is not limited to the above construction and may be constructed of a single substrate to have the detector 21 and various integrated circuits or the like. Constructing the unit substrate 20 in this fashion makes it possible to dispense with the connector C1 and correspondingly reduce cost, and simplifies assembly of the apparatus. In addition, such construction reduces stray capacity, thus allowing characteristics of the detector 21, even those of the apparatus, to be improved as well.

Figure 4:
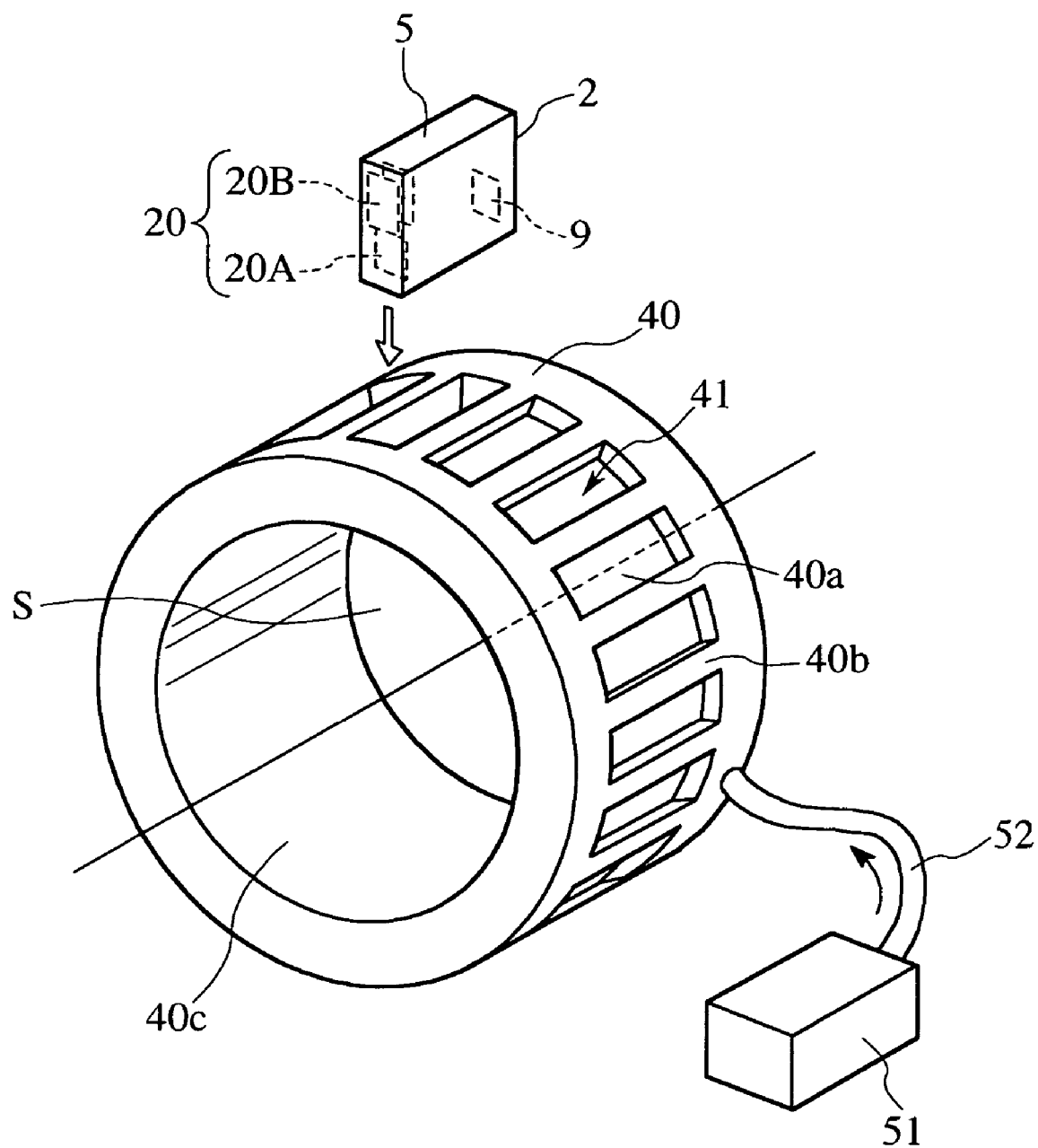
FIG. 4 is a perspective view showing a form of detector unit mounting in a unit-supporting section of the image acquisition device.

As shown in FIGS. 3A and 3B, and 4, the housing member 5 has a shape of a rectangular box with a space inside, and is installed circumferentially with respect to the ring-shaped unit-supporting section 40 (see FIG. 4) that is provided inside the casing 11A of the image acquisition device 11.

In the present embodiment, as described above, the unit substrates 20 accommodated in the housing member 5 are arranged in 15 rows at required intervals so as not to overlap one another at progressively deeper positions (i.e., in the longitudinal direction of the bed 14). In addition, multiple coupling substrates 22 are arranged with required intervals at a rear end of the housing member 5 (i.e., on the right in FIG. 3B). Four substrate/circuit board fixing bars 32 extend in a longitudinal direction of the housing member 5 (i.e., in the longitudinal direction of the bed 14) to as to span between the inner walls of the housing member 5. The fixing bars 32 support the signal processor substrates 20B by extending through respective portions near four corners of each signal processor substrate 20B, so that the unit substrates 20 and the coupling substrates 22 are supported in the housing member 5.

Also, a unit fan 33 for air exhaust is provided at an upper section of the housing member 5. The unit fan 33 incorporate fans each rotationally driven by a thin-walled motor not shown, and has a function to discharge internal air of the housing member 5 towards an exhaust duct 43 (see FIG. 2) that is provided thereabove (externally thereto). The unit fan 33 operates on the electric power supplied from the low-voltage power supply (not shown) that is connected to the coupling substrate 22. In addition, the unit fan 33 may be of a normally actuated type or may be constructed so as to operate by detecting the fact that an internal temperature of the housing member 5 has reached a required value. Electric power consumption can be suppressed by constructing the unit fan in this way.

Additionally, the housing member 5 internally has an adiabatic member 7 that functions as a partitioning member to segment the member 5 into a first region A in which the detector 21 is disposed, and a second region B in which the signal processor. The adiabatic member 7 is provided in a sealed-up condition with a required thickness in various spatial clearances S1. The spatial clearances S1 are formed, as shown in FIG. 3B, between unit substrates 20, between one unit substrate 20 and one coupling substrate 22, between one unit substrate 20 and an inner side face 5b of the housing member 5, and between one coupling substrate 22 and the inner side face 5b of the housing member 5, at the connector C1 positions of the unit substrates 20, and as shown in FIG. 3A, between one unit substrate 20 and inner side faces 5c of the housing member 5, and between one coupling substrate 22 and an inner side face of the housing member 5. That is to say, the adiabatic member 7 exists to segment the inside of the housing member 5 into an inner spatial clearance thereof (the first region A) in which all detectors 21 of the detector substrate 20A are positioned, and another inner spatial clearance thereof (the second region B) in which the signal processor substrate 20B and the coupling substrate 22 are positioned. The existence of the adiabatic member 7 makes it possible to prevent internal heat of the integrated circuits (such as digital ASIC 26) in the second region B from being propagated to the first region A, and hence to prevent the detector 21 from being exposed to high temperature.

A material, such as urethane, that is of low thermal conductivity and has an excellent filling-in property with respect to the spatial clearances S1 can be used as the adiabatic member 7. Preferably, the member 7 is made of the urethane wrapped up in an electromagnetic wave shielding member capable of shielding electromagnetic waves, for example, a metallic sheet. Use of such an electromagnetic wave shielding member allows protection of the detector 21 from the electromagnetic waves originating from the integrated circuits such as the digital ASIC 26. Thus, the detector 21 can be enhanced in time resolution and in energy resolution. Using alternatively an adiabatic member 7 made from a resilient material, for example, rubber, further simplifies the sealing-up of the spatial clearances S1. In addition, even if the unit substrate 20 vibrates during transport of the PET apparatus 1, the vibration can be appropriately suppressed.

Although a filling-in material for the adiabatic member 7 is used at the connector C1 of the unit substrate 20 in the foregoing example, this position of the filler is only an example and the filler may be provided at any position in which the heat generated from the integrated circuits such as the digital ASIC 26 can be prevented from being transferred to the detector 21. For example, the position of the filler in that case may be below and near the integrated circuits such as the digital ASIC 26.

As shown in FIG. 3B, the coolant discharging element 6 is constructed of a unit fan 33 and a large number of ventilation holes 34. The unit fan 33 forcibly discharges the internal air of the housing member 5 to the outside thereof and is provided at a 180°-opposite position with respect to each detector 21, with each signal processor substrate 20B being positioned between the fan unit 33 and detector 21 in the housing member 5. In other words, the unit fan 33 is positioned at an upper section of the housing member 5 shown in FIGS. 3A and 3B. Each ventilation hole 34 adapted to introduce cooling air from the outside of the detector unit 2 into the housing member 5 is formed in both inner side portions 5a of the member 5 in a lateral direction thereof (i.e., in a circumferential direction thereof in FIG. 2). Thus, cooling air is introduced from a lateral direction with respect to a face of each signal processor substrate 20B. In the present embodiment, four ventilation holes 34 are formed in each side portion 5a, along the signal processor substrate 20B. In addition, although not shown in FIG. 3B, the array of ventilation holes 34 shown in FIG. 3A is formed in multiple sets (e.g., as many as there actually are the signal processor substrates 20B and the coupling substrates 22) in a layout direction of the signal processor substrates 20B (i.e., in the longitudinal direction of the bed 14). This makes it possible to introduce an approximately uniform, desired amount of air into the housing member 5 and uniformly cool each signal processor substrate 20B and each coupling substrate 22.

Furthermore, in addition to being formed so as to communicate with the second region B of the housing member 5, each ventilation hole 34 is formed at a position near the detectors 21 (the first region A), in other words, at the position most distant from the unit fans 33. This makes it possible, as indicated by dashed lines in FIG. 5, to circulate cooling air evenly through the signal processor substrate 20B and the coupling substrate 22 in their entirety, and to raise cooling efficiency.

As shown in FIG. 3B, a ventilation port 8 is positioned at where it communicates with the first region A, in a longitudinal rear side portion 5d of the housing member 5. In addition, an anti-dust filter 9 is provided in such a form as to cover the entire ventilation port 8. The position of the ventilation port 8 having the anti-dust filter 9 is not limited to the longitudinal rear side portion 5d of the housing member 5 and may be in any other side portion thereof or at a lower portion 5e thereof. In addition, the ventilation port 8 with the anti-dust filter 9 may be provided in multiple places, not one place.

Examples of the element that can be used as the anti-dust filter 9 include a HEPA (High-Efficiency Particulate Air) filter. The anti-dust filter 9 is not limited to a type constructed of a single filter, and may be a combination of multiple kinds of filters. Additionally, the anti-dust filter 9 does not always need to be a HEPA filter and may be any other kind of filter, such as a type formed from paper, an unwoven cloth, or the like. Ingress of dust and the like from the outside of the housing member 5 into the first region A where a large number of detectors 21 are provided can be prevented by providing such an anti-dust filter 9 at the ventilation port 8 in the housing member 5. Furthermore, if the ventilation port 8 with the anti-dust filter 9 is provided on a side not opposite to an adjacent detector unit 2, this allows each detector unit 2 to be arranged more densely and detection sensitivity to be improved.

As shown in FIG. 4, the detector unit 2 with the thus-constructed housing member 5 is installed in the unit-supporting section 40 set up inside the casing 11A (see FIG. 2) of the image acquisition device 11. The unit-supporting section 40 is ring-shaped and has multiple openings 40a at required intervals in a circumferential direction of the supporting section 40, on an outer peripheral surface thereof. Also, the unit-supporting section 40 is constructed so that one detector unit 2 is inserted from the side of the detector substrate 20A of the unit substrate 20 into each opening 40a. Fixing the detector unit 2 to the unit-supporting section 40 is conducted using, for example, screws that are not shown. Thus, the detector unit 2 is constructed to be attachable and removable to and from the unit-supporting section 40, and maintenance and the like are facilitated.

In the present embodiment, since the housing members 5 of the adjacent detector units 2 are arranged close to one another at a very small angle, radiation detection sensitivity can be improved with a minimum quantity of γ-rays passing there through. Inspection time can therefore be reduced.

Figure 5:
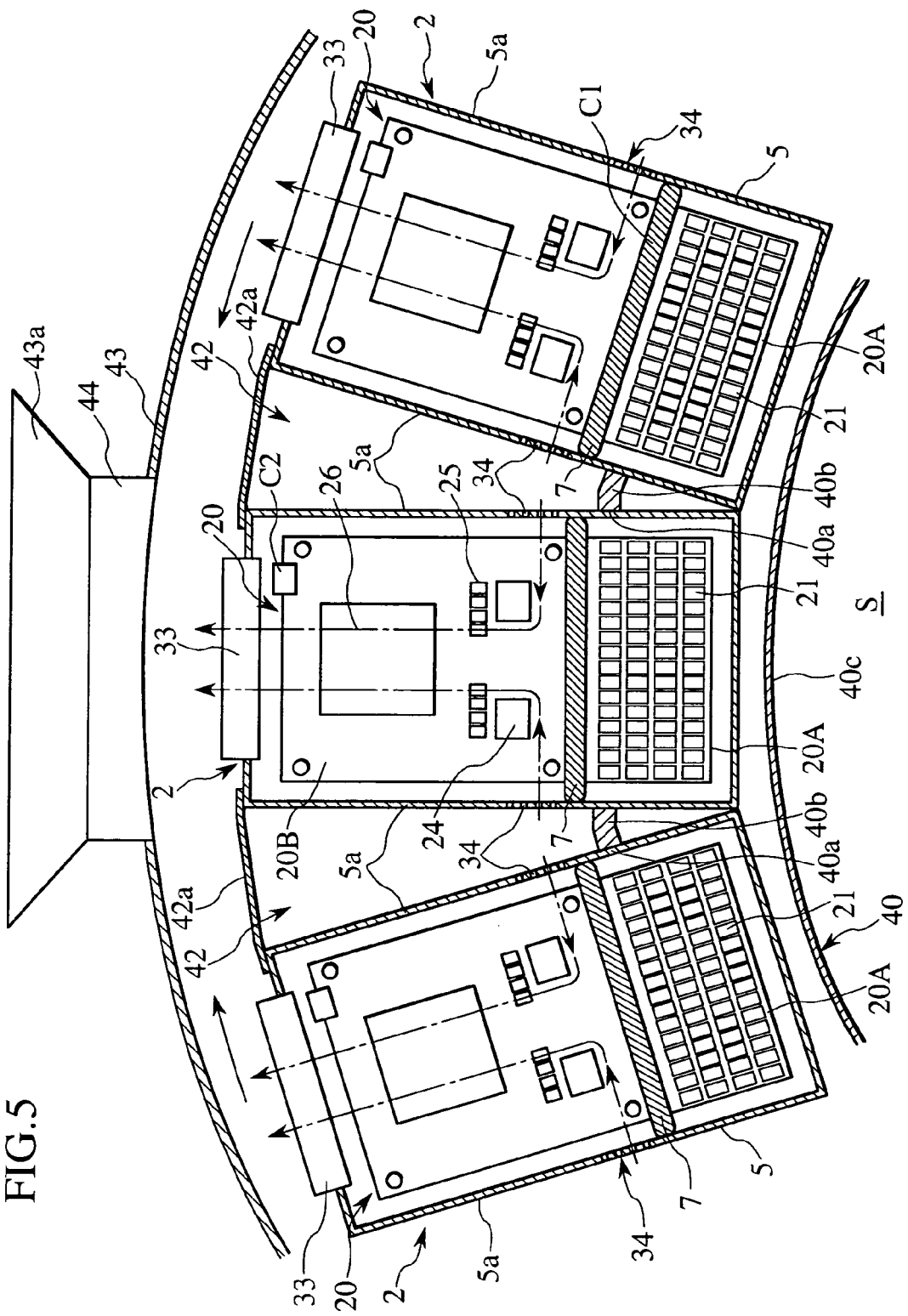
FIG. 5 is a sectional view of the detector units existing after being mounted in the unit-supporting section.

As shown in FIG. 2, the cooler 50 mainly includes an air blower 51, a duct 52 for introducing air from the blower 51 into the unit-supporting section 40, an air guideway 42, an air exhaust duct 43 provided so as to encircle the outside of the air guideway 42, and air exhaust fans 44 provided on the exhaust duct 43. The air guideway 42 is, as shown in FIG. 5, defined between an opening verge 40b, the side portions 5a of the housing members 5, and a top plate 42a spanned between the adjacent housing members 5 and is formed between the adjacent housing members 5.

The blower 51 and the duct 52 are installed outside the casing 11A. The blower 51 is disposed at a lateral or rear end (or the like) of the image acquisition device 11 or at any other location unobtrusive to, for example, operation or maintenance of the image acquisition device 11. The blower 51 uses a built-in fan to take in air from a room in which the image acquisition device 11 is installed, and supplies the air to the air guideway 42 through the duct 52 first and then a flow passageway not shown. An air-cleaning filter not shown is installed on an air intake side of the blower 51, and air that has passed through the air-cleaning filter is used as cooling air. This air-cleaning filter can be a HEPA filter of high dust-collecting performance, an electric type of dust-collecting filter, or the like.

The air guideway 42 communicates with the second region B inside the housing member 5 via the ventilation hole 34 in the side portion 5a of the housing member 5. When the unit fan 33 inside the housing member 5 is driven, air from the air guideway 42 is introduced into the housing member 5. The exhaust duct 43 communicates with the inside of the housing member 5 via the unit fan 33, and the air inside the housing member 5 is discharged towards the exhaust duct 43 by the driving of the unit fan 33. The exhaust hole 43a opened in the installation room of the image acquisition device 11 is provided in a total of three places in the exhaust duct 43, and the air inside the exhaust duct 43 is discharged into the room through the exhaust fans 44 at the exhaust holes 43a.

While the present embodiment is constructed so that the air inside the installation room of the image acquisition device 11 is used as cooling air, and re-discharged into an examination room after cooling, the present invention may be adapted to take in air from an exterior of the examination room and re-discharge the air therefrom after cooling.

Next, operation of the PET apparatus 1 of the present embodiment is described. When electric power is supplied to the image acquisition device 11 by power supply switch operations, the blower 51, the unit fans 33 and the exhaust fan 44 operate synchronously with operation of the image acquisition device 11. Cooling air is sent from the blower 51 via the duct 52 to the air guideway 42 in the unit-supporting section 40, and the sent cooling air is introduced into the second region B of each housing member 5 through each ventilation hole 34 in the side portion 5a of the housing member 5. At this time, since the unit fans 33 are driven and the air in the second region B of the housing member 5 is forcibly discharged, the air in the second region B of the housing member 5 flows from the ventilation hole 34, towards the unit fan 33, as indicated by the dashed lines in FIG. 5. This flow of the air cools the integrated circuits such as the analog ASICs 24, thus allowing a temperature rise of the second region B to be suppressed.

Cooling air that has been supplied to the inside of the housing member 5 is forcibly discharged into the exhaust duct 43. The after-cooling air, after being discharged from the exhaust duct 43, is re-discharged from the exhaust hole 43a into the room by the exhaust fan 44 provided at the exhaust hole 43a. In this way, the cooler 50 conducts cooling using cooling air.

On the air intake side connected to the unit-supporting section 40, the cooler 50 has a filter not shown, and this filter prevents dust of a relatively large particle size from being introduced into the image acquisition device 11. The filter is provided because an attempt to remove dust of a particle size smaller than necessary lowers an aperture ratio, resulting in a passage of air that is not smooth and thus results in reduced cooling capability. Accordingly, dust that is too small in particle size for the filter within the cooler 50 to remove will circulate through each detector unit 2. Consequently, the inside of the detector unit 2 will be laden with dust in the second region B during an extended time of operation. The housing member 5 is internally segmented into the first region A having the detectors 21 arranged therein, and the second region B accommodating the analog ASICs 24 (signal processors) and other integrated circuits. During actual operation, however, it is impossible to completely shield the first region A and the second region B, in other words, to completely block the flow of air. Formation of very small clearances may therefore occur, for example, between the adiabatic member 7 and the unit substrate 20, between the adiabatic member 7 and the coupling substrate 22, between the adiabatic member 7 and the inner side faces 5b of the housing member 5, and between the adiabatic member 7 and internal corners of the housing member 5. In other cases, deterioration of the adiabatic member 7 itself, for example, may form such minute clearances as mentioned above. If the housing member 5 does not have the ventilation port 8 (see FIGS. 3A and 3B) in the present embodiment, the flow of air (upward air current) occurring in the second region B, as shown in FIG. 5, will cause the air in the second region B to be taken in via the above-mentioned clearances during the operation of the unit fan 33, and result in the inside of the second region B being filled with a negative pressure. If the unit fan 33 stops operating after that, the air in the second region B will immediately flow into the first region A. The flow of the air into the first region A, therefore, will also cause a simultaneous inflow of the dust that has accumulated in the second region B. This inflow of the dust will cause dust to stick to the detectors 21, hence resulting in a problem in that the detectors 21 characteristics would deteriorate.

In addition, the entire examination room, with the PET apparatus 1 placed therein, is air-conditioned for low-humidity air to be incorporated into the detector units 2 during the operation of the PET apparatus 1. Therefore, if the present embodiment does not include the ventilation port 8 and the first region A is maintained in an incompletely enclosed condition by the presence of the foregoing minute clearances, humidity in the first region A with the detectors 21 provided therein will not immediately reach the value set by air-conditioning. The result would be that the humidity would become difficult to control. Even if humidity control is possible, a long time would be required for the humidity to reach its setting.

For these reasons, in the present embodiment, providing the ventilation port 8 in the position where it communicates with the first region A of the housing member 5 makes it possible to prevent the first region A from being filled with a negative pressure. It is therefore possible to prevent the flow of air from the second region B via very small clearances into the first region A during the operational stop of the unit fan 33, and thus to prevent accumulated dust in the second region B from entering the first region A. Accordingly, it is possible to avoid the inconvenience of the radiation detectors 21 being degraded in performance.

In the present embodiment, the ingress of dust from the above-mentioned ventilation port 8 can also be prevented since an anti-dust filter 9 is installed so as to cover the entire ventilation port 8. In addition, the installation of the anti-dust filter 9 makes the first region A enter a state equal to an essentially open state, and allows the first region A to be adjusted to the humidity set by air-conditioning. Hence, humidity control of the first region A becomes easy.

While the present embodiment uses semiconductor radiation detectors as the radiation detectors, the present invention is not limited to the use of this detector type and for example, scintillators may be used instead. If scintillators are used as the radiation detectors, the signal processors in that case can each be constructed of a photomultiplier and a position arithmetic device or the like. In this case, dust-proofing and moisture-proofing effects can likewise be obtained if a ventilation hole with an anti-dust filter is provided in each housing member that shrouds one such scintillator.

In addition, since the detectors 21 in which the CdTe used in the present embodiment is employed as their semiconductor material react with light to generate an electric charge, optical shielding is preferably provided to prevent each such detector 21 from being irradiated with incoming external light. More specifically, the housing member 5 and unit-supporting section 40 shown in FIG. 4 are both constructed of an optical-shielding material such as aluminum or aluminum alloy, and are adapted so that there are no clearances permitting entry of light, including fit-in sections between both the housing member 5 and the unit-supporting section 40.

The light coming in from a direction of the space S can be reliably prevented from reaching the detectors 21, by disposing a cylindrical plate 40C such that an outer peripheral surface is positioned near a lower end of the housing member 5. In addition, optical shielding performance can be improved by constructing the cylindrical plate 40c from an aluminum alloy (or aluminum). Furthermore, the light coming in from the direction of the space S can likewise be shielded by adopting a construction in which the housing member 5 is shrouded with, for example, an optical shielding cover (not shown). Alternatively, instead of using the optical shielding cover, or the like, the detectors 21 could be coated with an optical shielding material so as to form an optical shielding film.

Next, another aspect of a cooler will be described referring to FIGS. 6 and 7. A cooler 50A is constituted by an introducing member 60 and a discharging member 70.

Figure 6:
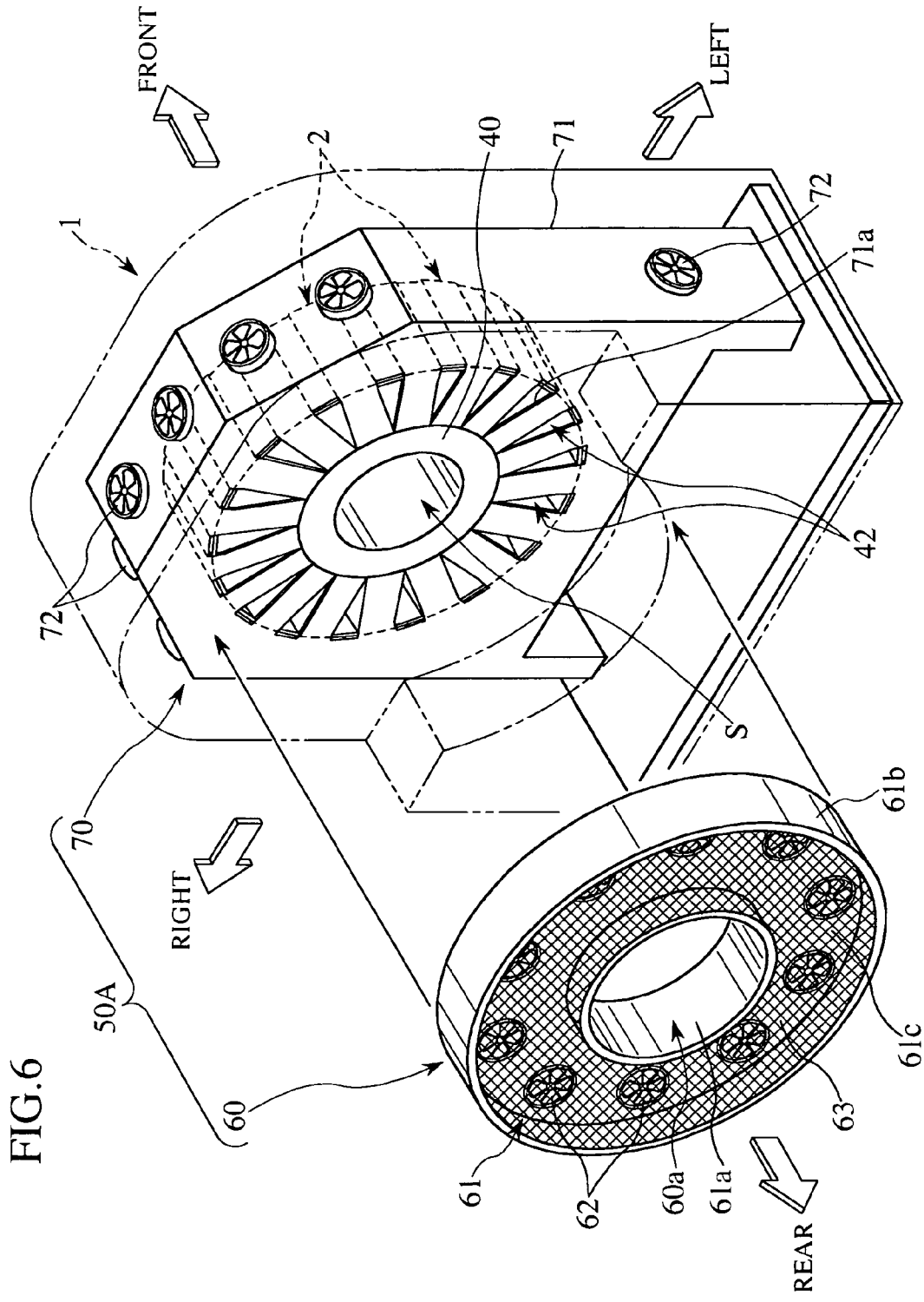
FIG. 6 is an exploded perspective view showing a modification of a cooler.
Figure 7:
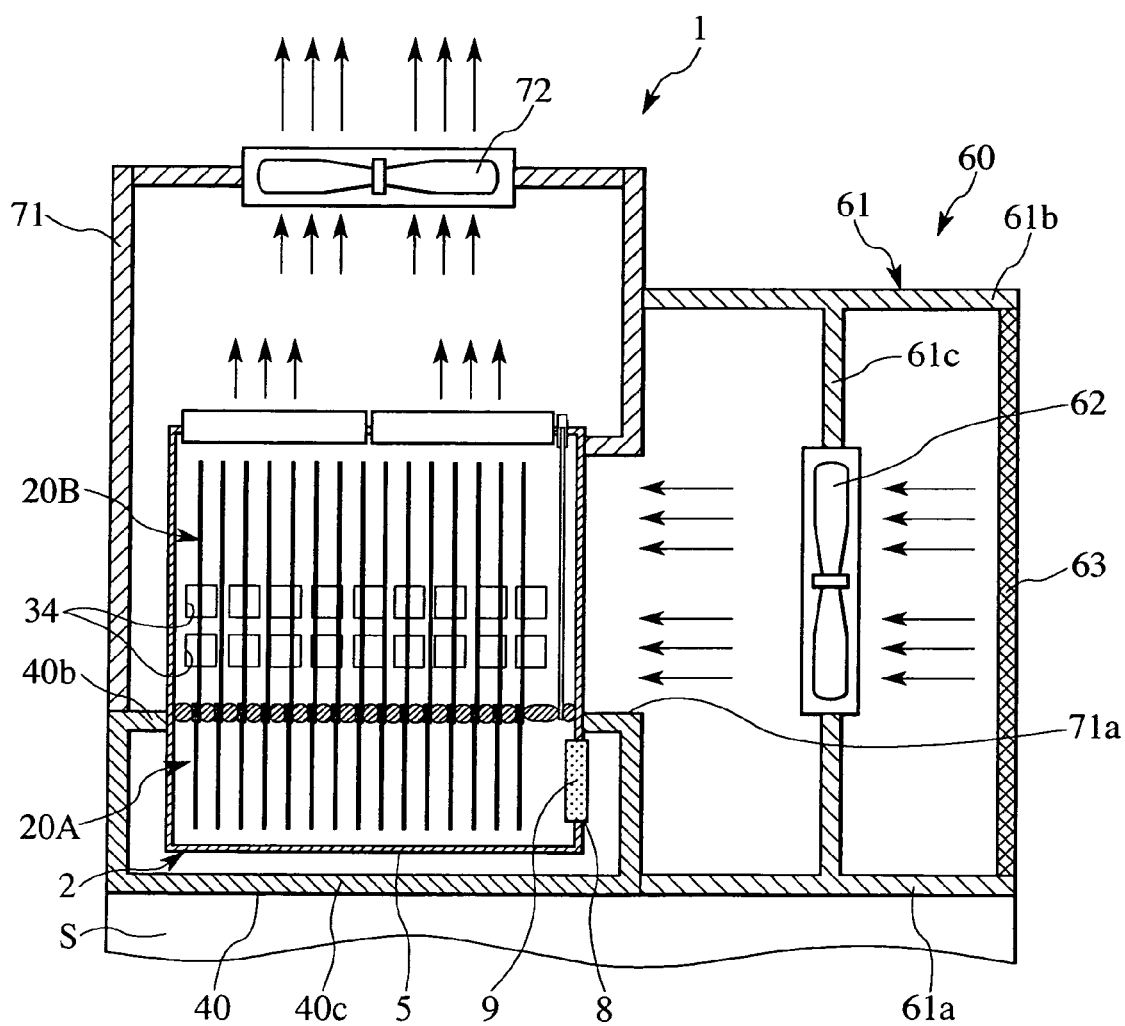
FIG. 7 is a sectional view of the modification of the cooler.

The introducing member 60 is, as shown in FIG. 6, provided on a rear panel side of the PET apparatus 1 and assumes an annular form to cover an entire rear panel side of the unit-supporting section 40. Also, the introducing member 60 includes a ring-shaped inner pipe 61a, a ring-shaped outer pipe 61b, a shielding section 61c coupling the inner pipe 61a and the outer pipe 61b with each other, multiple air intake fans 62, and a filter 63. The inner pipe 61a and the outer pipe 61b are formed with the same required length in a longitudinal direction. The shielding section 61c is coupled with both the inner pipe 61a and the outer pipe 61b, at an intermediate position (see FIG. 7) in the longitudinal direction thereof. Each air intake fan 62 is provided circumferentially with respect to the shielding section 61c. The filter 63 for preventing ingress of the dust contained in the air coming in from the outside of the PET apparatus 1 is disposed so as to cover the entire ring-shaped region sandwiched between the inner pipe 61a and the outer pipe 61b, on the rear panel side of the PET apparatus 1. Thus, cooling air, from which has been removed the large-grain-size dust taken in from the outside of the PET apparatus 1, is introduced into an introducing section 71a. Additionally, providing the multiple air intake fans 62 in the layout direction of the detector units 2 makes it possible to supply a uniform amount of cooling air to each air guideway 42 and cool each detector unit 2 uniformly.

The discharging member 70 includes a frame 71 that covers each detector unit 2, and multiple exhaust fans 72. The frame 71 assumes a shape in which it shrouds the outside of each detector unit 2 protruding from the above-mentioned unit-supporting section 40. In the frame 71, a space is also formed that extends from the opening verge 40b (see FIG. 7) of the unit-supporting section 40 and functioning as a passageway for air to flow outward with respect to the unit fan 33 of the detector unit 2 (i.e., towards an upper section of FIG. 7). In addition, an introducing section 71a communicating with each air guideway 42 described above is formed on a rear panel side of the frame 71. The exhaust fans 72 are, as shown in FIG. 6, spaced from each other in the layout direction of the detector units 2, on an outer surface of the frame 71. Providing multiple exhaust fans 72 in this form makes it possible to efficiently discharge exhaust air from each detector unit 2 to the exterior of the PET apparatus 1.

Advantageous effects of the present embodiment are described below.

(1) According to the present embodiment, since the housing member 5, communicating with the first region A in which the detectors 21 are accommodated, has a ventilation port 8 equipped with an anti-dust filter 9, it is possible to prevent dust from sticking to each detector (semiconductor radiation detector) 21, thus preventing the detector 21 from deteriorating in characteristics. Therefore, time-varying changes in apparatus characteristics can be suppressed and frequency of apparatus maintenance can be significantly reduced.

(2) According to the present embodiment, since the housing member 5 communicating with the first region A in which the detectors 21 are accommodated has a ventilation port 8 equipped with an anti-dust filter 9, it is possible to facilitate humidity control of the detectors 21, stabilize the characteristics thereof, that is, apparatus characteristics, and improve diagnosing accuracy.

(4) According to the present embodiment, during substrate/circuit board replacement and other servicing operations, very high maintainability can be achieved since the integrated circuits (analog ASICs 24, ADCs 25, and digital ASIC 26) that are most likely to suffer from a failure, compared with other sections, are mounted on each signal processor substrate 20B, since the detectors 21 are mounted on each detector substrate 20A, and since each coupling substrate 22 is removable from the housing member 5 of the detector unit 2.

(5) According to the present embodiment, the anti-dust filters to be used on the intake side of the cooling air supplied from the cooler 50 to the image acquisition device 11, and on the side near the first region A, can be filters that are different with respect to dust-collecting performance. In other words, a coarse-meshed filter of low dust-collecting performance and a fine-meshed filter of high dust-collecting performance can be used on the intake side and the side near the first region A, respectively. The use of the two kinds of filters makes it possible to appropriately protect circuit elements and the detectors 21 from dust without reducing the capability for each detector unit 2. In addition, since using a coarse-meshed filter on the intake side allows pressure loss to be reduced and the unit fans 33 and exhaust fans 44 in the image acquisition device 11 to be reduced in quantity and in fan speed, electric power consumption is reduced and an operating sound level of the apparatus is significantly lowered.

(6) According to the present embodiment, by heat-insulating, not only the signal processors that generate heat, but also the detectors 21 that do not generate heat but are to be maintained at low temperature, it is possible to suppress a temperature rise of the detectors 21. This improves the detectors 21 in time resolution and in energy resolution, thus leading to improved quality and quantitative characteristics of the image obtained from the PET apparatus 1, and to improved diagnosing accuracy.

(7) According to the present embodiment, since each detector substrate 20A and each signal processor substrate 20B are connected by a connector C1 as independent substrates, it is possible to suppress heat conduction from the signal processor system to the detectors 21 and hence to minimize a temperature rise of the detectors 21. This further improves the quality and quantitative characteristics of the image obtained from the PET apparatus 1, and thus further improves diagnosing accuracy.

(8) According to the present embodiment, since a temperature rise of the detectors 21 can be minimized, the characteristics thereof are stabilized (time-varying changes are reduced and a failure rate is lowered), reliability of the PET apparatus 1 improves, and running costs can be lowered.

While, in the present embodiment, the inside of each detector unit 2 is segmented into the first region A where the detectors 21 are accommodated, and the second region B where the signal processors are accommodated, the present invention is not limited thereto and the segmentation may be performed by inserting a sponge-like material between unit substrates 20, between one unit substrate 20 and one coupling substrate 22, between one unit substrate 20 and one housing member 5, and between one coupling substrate 22 and one housing member 5.

In the present embodiment, the housing member itself may be formed integrally with both the first region A and the second region B, instead of the adiabatic member 7 or any other independent member being used. That makes it possible to reduce the number of components required.

While the present embodiment has been described taking the adiabatic member 7 as an example of the member for implementing the segmentation into the first region A and the second region B, the present invention is not limited to this example and using a conductive material, instead of the adiabatic member 7, allows the electromagnetic waves emitted from the signal processors to be stopped from propagating to the detectors 21.

While the invention has been described in its preferred embodiments, it is to be understood that the words which have been used are words of description rather than limitation and that changes within the purview of the appended claims may be made without departing from the true scope and spirit of the invention in its broader aspects.

What is claimed is:

1. A nuclear medicine diagnostic apparatus with detector units arranged around a bed on which to hold a human body examined, the detector units each comprising:
    a plurality of unit substrates each including a plurality of radiation detectors for detecting radiation, and a plurality of signal processors to each of which an independent detection signal from each of the radiation detectors is input;
    a housing member having the plurality of unit substrates, the housing member being segmented into a first region in which the plurality of radiation detectors are disposed, and a second region in which the plurality of signal processors are disposed; and
    means for first introducing a gaseous coolant into only the second region through a ventilation hole in order to cool the plurality of signal processors, and then discharging the coolant from the second region;
    wherein the housing member is formed with a ventilation port to communicate with an exterior of the housing member as well as with the first region, the housing member also having an anti-dust filter connected to the ventilation port.

2. A nuclear medicine diagnostic apparatus with detector units arranged around a bed on which to hold a human body examined, the detector units each comprising:
    a plurality of unit substrates each including a plurality of radiation detectors for detecting radiation, and a plurality of signal processors to each of which an independent detection signal from each of the radiation detectors is input;
    a housing member having the plurality of unit substrates;
    a partitioning member for segmenting a space into a first region in which the plurality of radiation detectors are disposed, and a second region in which the plurality of signal processors are disposed; and
    means for first introducing a gaseous coolant into only the second region through a ventilation hole in order to cool the plurality of signal processors, and then discharging the coolant from the second region;
    wherein the housing member is formed with a ventilation port to communicate with an exterior of the housing member as well as with the first region, the housing member also having an anti-dust filter connected to the ventilation port.

3. The nuclear medicine diagnostic apparatus according to claim 2, wherein the partitioning member is an adiabatic member.

4. The nuclear medicine diagnostic apparatus according to claim 2, wherein the partitioning member is an electromagnetic wave shielding member.

5. The nuclear medicine diagnostic apparatus according to claim 1, wherein the ventilation port with the anti-dust filter is provided on a side not facing an adjacent detector unit.

6. The nuclear medicine diagnostic apparatus according to claim 1, wherein:
    the ventilation hole being positioned near the plurality of radiation detectors;
    the means for first introducing and then discharging the has a fan that discharges the coolant from the second region; and
    the fan is provided on a side facing the plurality of radiation detectors, across the plurality of signal processors.

7. The nuclear medicine diagnostic apparatus according to claim 1, wherein the plurality of radiation detectors and the plurality of signal processors are provided on a single substrate.

8. The nuclear medicine diagnostic apparatus according to claim 1, wherein:
    the plurality of radiation detectors are provided on a first substrate; and
    the plurality of signal processors are provided on a second substrate coupled with the first substrate via a connector.

9. The nuclear medicine diagnostic apparatus according to claim 8, wherein the ventilation hole is constructed such that the gaseous coolant is introduced from a lateral direction with respect to a face of the second substrate.

10. The nuclear medicine diagnostic apparatus according to claim 1, wherein the plurality of radiation detectors are semiconductor radiation detectors.

11. The nuclear medicine diagnostic apparatus according to claim 1, wherein the housing member has an optical shielding property.

12. A positron emission tomography apparatus with detector units arranged around a bed on which to hold the human body examined, the detector units each comprising:
    a plurality of unit substrates each including a plurality of radiation detectors for detecting radiation, and a plurality of signal processors to each of which an independent detection signal from each of the radiation detectors is input;
    a housing member having each of the plural unit substrates;
    a partitioning member for segmenting a space into a first region in which the plurality of radiation detectors are disposed, and a second region in which the plurality of signal processors are disposed; and
    means for first introducing a gaseous coolant into only the second region through a ventilation hole in order to cool the plurality of signal processors, and then discharging the coolant from the second region;
    wherein the housing member is formed with a ventilation port to communicate with an exterior of the housing member as well as with the first region, the housing member also having an anti-dust filter connected to the ventilation port.

13. A detector unit comprising:
    a plurality of unit substrates each including a plurality of radiation detectors for detecting radiation, and a plurality of signal processors to each of which an independent detection signal from each of the radiation detectors is input;
    a housing member having the plurality of unit substrates, the housing member segmenting a space into a first region in which the plurality of radiation detectors are disposed, and a second region in which the plurality of signal processors are disposed; and means for first introducing a gaseous coolant into only the second region through a ventilation hole in order to cool the plurality of signal processors, and then discharging the coolant from the second region;

wherein the housing member is formed with a ventilation port to communicate with an exterior of the housing member as well as with the first region, the housing member also having an anti-dust filter connected to the ventilation port.

14. A detector unit comprising:

a plurality of unit substrates each including a plurality of radiation detectors for detecting radiation, and a plurality of signal processors to each of which an independent detection signal from each of the radiation detectors is input;

a housing member having the plurality of unit substrates;

a partitioning member for segmenting a space into a first region in which the plurality of radiation detectors are disposed, and a second region in which the plurality of signal processors are disposed; and means for first introducing a gaseous coolant into only the second region through a ventilation hole in order to cool the plurality of signal processors, and then discharging the coolant from the second region;

wherein the housing member is formed with a ventilation port to communicate with an exterior of the housing member as well as with the first region, the housing member also having an anti-dust filter connected to the ventilation port.

15. The detector unit according to claim 14, wherein the partitioning member has an adiabatic property.

16. The detector unit according to claim 14, wherein the partitioning member is formed of a material that shields electromagnetic waves.

17. The detector unit according to claim 13, wherein:

the ventilation hole being positioned near the plurality of radiation detectors; and the means for first introducing and then discharging the coolant has a fan that discharges the coolant from the second region; and the fan is provided on a side facing the plurality of radiation detectors, across the plurality of signal processors.

18. The detector unit according to claim 13, wherein the plurality of radiation detectors and the plurality of signal processors are provided on a single substrate.

19. The detector unit according to claim 13, wherein:

the plurality of radiation detectors are provided on a first substrate; and the plurality of signal processors are provided on a second substrate coupled with the first substrate via a connector.

20. The nuclear medicine diagnostic apparatus according to claim 1, wherein the ventilation port is provided to prevent a negative pressure from being formed in the first region so as to prevent dust from flowing from the second region into the first region.

21. The nuclear medicine diagnostic apparatus according to claim 2, wherein the ventilation port is provided to prevent a negative pressure from being formed in the first region so as to prevent dust from flowing from the second region into the first region.

22. The positron emission tomography apparatus according to claim 12, wherein the ventilation port is provided to prevent a negative pressure from being formed in the first region so as to prevent dust from flowing from the second region into the first region.

23. The detector unit according to claim 13, wherein the ventilation port is provided to prevent a negative pressure from being formed in the first region so as to prevent dust from flowing from the second region into the first region.

24. The detector unit according to claim 14, wherein the ventilation port is provided to prevent a negative pressure from being formed in the first region so as to prevent dust from flowing from the second region into the first region.

* * * * *